US010365193B2

(12) United States Patent
Feng et al.

(10) Patent No.: US 10,365,193 B2
(45) Date of Patent: Jul. 30, 2019

(54) TEST APPARATUS AND METHOD FOR DETERMINING TIME-DEPENDENCE FAILURE UNDER CONSTANT TEMPERATURE THROUGH HIGH PRESSURE TRUE TRIAXIAL LOADING FOR HARD ROCK

(71) Applicant: Northeastern University, Shenyang, Liaoning Province (CN)

(72) Inventors: Xia ting Feng, Shenyang (CN); Xi wei Zhang, Shenyang (CN); Cheng xiang Yang, Shenyang (CN); Shuai Peng, Shenyang (CN); Jun Tian, Shenyang (CN); Rui Kong, Shenyang (CN); Dong hui Ma, Jilin Province (CN)

(73) Assignee: NORTHEASTERN UNIVERSITY, Shenyang, Liaoning Province (CN)

( * ) Notice: Subject to any disclaimer, the term of this patent is extended or adjusted under 35 U.S.C. 154(b) by 187 days.

(21) Appl. No.: 15/563,358

(22) PCT Filed: Jan. 17, 2017

(86) PCT No.: PCT/CN2017/071400
§ 371 (c)(1),
(2) Date: Sep. 29, 2017

(87) PCT Pub. No.: WO2018/113063
PCT Pub. Date: Jun. 28, 2018

(65) Prior Publication Data
US 2018/0313727 A1    Nov. 1, 2018

(30) Foreign Application Priority Data

Dec. 20, 2016    (CN) .......................... 2016 1 1187101

(51) Int. Cl.
*G01N 3/12*    (2006.01)
*G01N 3/10*    (2006.01)

(52) U.S. Cl.
CPC ....... *G01N 3/12* (2013.01); *G01N 2203/0019* (2013.01); *G01N 2203/0048* (2013.01); *G01N 2203/0067* (2013.01); *G01N 2203/0222* (2013.01); *G01N 2203/0232* (2013.01); *G01N 2203/0256* (2013.01)

(58) Field of Classification Search
CPC ............. G01N 3/12; G01N 2203/0019; G01N 2203/0048; G01N 2203/0067; G01N 2203/0232; G01N 2203/0256
(Continued)

(56) References Cited

U.S. PATENT DOCUMENTS

| 3,975,950 | A | * | 8/1976 | Erdei | ........................ | G01N 3/10 73/790 |
| 5,025,668 | A | * | 6/1991 | Sarda | ........................ | G01N 3/10 73/795 |
| 9,410,874 | B2 | * | 8/2016 | He | ........................ | G01N 3/313 |

FOREIGN PATENT DOCUMENTS

| CN | 102735532 A | 10/2012 |
| CN | 102735548 A * | 10/2012 |

(Continued)

OTHER PUBLICATIONS

Office Action dated Dec. 12, 2018 in corresponding CN Application 201611187101.X and English translation thereof, 11 pages.

*Primary Examiner* — Leslie J Evanisko
*Assistant Examiner* — Ruben C Parco, Jr.
(74) *Attorney, Agent, or Firm* — Muncy, Geissler, Olds & Lowe P.C.

(57) ABSTRACT

An apparatus and method for determining time-dependence failure under constant temperature through high pressure true triaxial loading for hard rock, includes a pressure chamber and four actuators, wherein a sample bearing (Continued)

platform is arranged in a center of the pressure chamber, a sample bearing and containing chamber is arranged in a center of the sample bearing platform, and a confining pressure loading oil supply hole is formed in the sample bearing platform, and communicates with a confining pressure loading injection pump; each actuator includes a sealing cover, an annular end cover, a counter-force cylinder barrel, a piston, a piston rod, a sealing flange and a stress loading injection pump; a heating coil is arranged in the pressure chamber; a force sensor is fixedly mounted at the end part of the piston rod; and a pressure sensor is mounted in the sample bearing platform.

9 Claims, 9 Drawing Sheets

(58) Field of Classification Search
USPC .................................................. 73/819, 812
See application file for complete search history.

(56) References Cited

FOREIGN PATENT DOCUMENTS

| CN | 204613077 U | 9/2015 | |
|----|----|----|----|
| CN | 105300807 A | 2/2016 | |
| CN | 105547849 A | 5/2016 | |
| KR | 101654303 B1 | 9/2016 | |
| WO | WO-03074263 A1 * | 9/2003 | ........... B30B 11/005 |

* cited by examiner

TEST APPARATUS AND METHOD FOR DETERMINING TIME-DEPENDENCE FAILURE UNDER CONSTANT TEMPERATURE THROUGH HIGH PRESSURE TRUE TRIAXIAL LOADING FOR HARD ROCK

BACKGROUND OF THE INVENTION

1. Field of the Invention

The present invention belongs to the technical field of laboratory rock rheological tests and particularly relates to a test apparatus and method for determining time-dependence failure under constant temperature through high pressure true triaxial loading for hard rock.

2. The Prior Arts

Deep rock masses, which are served as natural carriers of engineering objects such as underground mining, deep tunnel and underground cavity excavation, petroleum and natural gas, and non-conventional energy exploitation, subjected to unequal geo-stress in three orthogonal directions at different levels, namely: a maximum principle stress, an intermediate principal stress and a minimum principal stress; and the bigger the buried depth is, the more complex a geological condition is, and the higher the magnitudes of the geo-stress are. The initial stress state of the rock masses is changed continuously when the rock masses are excavated, which possibly causes instantaneous cracking or time-dependence failure of the rock masses; the time-dependence failure of the rock masses under a condition of long-time loading belongs to the scope of rock rheology and is one difficulty in research on rock mechanics, and the time-dependence strength of rocks is directly related to safety during operation of engineering.

At present, research on long-time time-dependence failure of the rocks still remains at the primary stage; usually, a conventional rock triaxial rheological tester is adopted for research on the time-dependence failure of the rocks; and because only one special stress condition that the intermediate principal stress is equal to the minimum principal stress can be considered, but a true triaxial geo-stress boundary condition cannot be restored, and result application does not have representativeness. Additionally, the ground temperature of the deep rock masses is generally increased with the buried depth; usually, if the buried depth is increased by 100 m, the ground temperature is increased by 3 DEG C.; and the ground temperature is usually about 60 DEG C. in rock masses being 2000 m under the ground. For a conventional rock triaxial rheological tester, in order to reduce deformation of a rock sample caused by fluctuation of environment temperature, an indoor air conditioner is usually adopted for temperature control, or a temperature control apparatus with the temperature control accuracy of ±0.5 DEG C. is adopted for constant temperature control, but since the rheological deformation of a hard rock under a stress condition becomes smaller and is easier to affect by thermal deformation caused by slight temperature fluctuation, and the given stress condition and environment temperature do not conform to an actual stress condition and environment temperature obviously in a hard rock time-dependence failure test, so that the credibility of a test result is not high.

Therefore, it is necessary to promote the hard rock time-dependence failure test to a true triaxial condition. Whether the conventional rock triaxial rheological tester can be transformed into a rock true triaxial rheological tester, or whether the existing true triaxial equipment can be transformed into the true triaxial rheological tester? The answer is No. The specific reasons are as follows: for the conventional rock triaxial rheological tester, since an independent servo loading control technology for the intermediate principal stress is complex, a volume change measurement apparatus of the rock sample is conflicted with the space of a pressure chamber, the conventional rock triaxial rheological tester cannot be simply transformed into the rock true triaxial rheological tester; and for the existing triaxial equipment, a cooperative working mode of a hydraulic oil pump and an electro-hydraulic servo valve is usually adopted, a rock static stress-strain mechanical behaviour is obtained, the test cycle is within several hours generally, while the cycle of the hard rock time-dependence failure test is 3-6 months usually, it is assumed that the existing true triaxial equipment is forced to perform the hard rock time-dependence failure test for 3-6 months, hydraulic elements such as the hydraulic oil pump and the electro-hydraulic servo valve are seriously damaged, and the situation is not allowed apparently. In addition, a force sensor in the existing true triaxial equipment is usually arranged outside the pressure chamber, and the force sensor not only is influenced by the fluctuation of the environment temperature, but also in influenced by the friction of a force-transferring piston, so that the influence on load stable control can be caused.

Therefore, since being influenced by the condition that a loading boundary condition of the conventional rock triaxial rheological tester does not conform to an actual boundary condition and the restrained by that the existing true triaxial equipment does not have long-time stable loading capacity, the hard rock time-dependence failure test under the true triaxial condition is difficult to realize at present.

SUMMARY OF THE INVENTION

For the problems existing in the prior art, the present invention provides a test apparatus and method for determining time-dependence failure under constant temperature through high pressure true triaxial loading for hard rock, so that a rock time-dependence failure test under a true triaxial condition is realized for the first time, long-time stable loading capacity is achieved, and setting for constant temperature for an environment temperature condition can be realized.

In order to realize the purpose, the present invention adopts the following technical scheme: a high-pressure true triaxial hard rock constant-temperature time-dependence failure test apparatus, includes: a pressure chamber, a first maximum principle stress actuator, a second maximum principle stress actuator, a first intermediate principle stress actuator, a second intermediate principle stress actuator and a rigid support platform, wherein the pressure chamber is fixedly mounted on the rigid support platform, the first maximum principle stress actuator and the second maximum principle stress actuator are horizontally and symmetrically arranged on the left side and the right side of the pressure chamber, and the first intermediate principle stress actuator and the second intermediate principle stress actuator are arranged vertically and symmetrically on the upper side and the lower side of the pressure chamber, and wherein, a cylindrical through hole penetrating horizontally is formed in a center of the pressure chamber, four stress loading through holes are uniformly distributed in a rigid shell of the pressure chamber, on the upper side, the lower side, the left side and the right side of the cylindrical through hole, a cylindrical sample bearing platform is arranged in the cylindrical through hole, and is matched with the cylindrical through hole in a sealing manner, and the cylindrical sample bearing platform has axial movement freedom degrees relative to the cylindrical through hole; a sample bearing and containing chamber is arranged in the center of the cylindrical sample bearing platform, four rigid pressure head placing holes are uniformly distributed in the cylindrical sample bearing platform, on the upper side, the lower side, the left side and the right side of the sample bearing and containing chamber, the four rigid pressure head placing holes are in one-to-one correspondence to the four stress loading through holes, and a rigid pressure head is arranged in each of the four rigid pressure head placing holes; a confining pressure loading oil supply hole is formed on the cylindrical sample bearing platform and communicates with the sample bearing and containing chamber; the confining pressure loading oil supply hole communicates with a confining pressure loading injection pump; the first maximum principle stress actuator, the second maximum principle stress actuator, the first intermediate principle stress actuator and the second intermediate principle stress actuator have the same structure, and any of the first maximum principle stress actuator, the second maximum principle stress actuator, the first intermediate principle stress actuator and the second intermediate principle stress actuator includes: a sealing cover, an annular end cover, a counter-force cylinder barrel, a piston, a piston rod, a sealing flange and a stress loading injection pump, wherein the counter-force cylinder barrels are fixedly connected to the outer surface of the pressure chamber and are coincided with axial center lines of the stress loading through holes; the sealing cover is fixedly mounted at the middle of the annular end cover, the annular end cover is fixedly mounted at the outer end of the counter-force cylinder barrel, the sealing flange is fixedly mounted between the inner end of the counter-force cylinder barrel and the pressure chamber, one end of the piston rod is located in the counter-force cylinder barrel, the other end of the piston rod penetrates through the sealing flange and extends into the stress loading through holes, the piston is located in the counter-force cylinder barrel and is fixedly arranged on the piston rod in a sleeving manner, and the piston is matched with the counter-force cylinder barrel in a sealing and sliding manner; a stress loading oil supply hole is formed on the annular end cover, a stress loading oil chamber is arranged between the annular end cover and the piston, and the stress loading oil supply hole communicates with the stress loading oil chamber; a stress unloading oil supply hole is formed on the counter-force cylinder barrel, a stress unloading oil chamber is arranged between the piston and the sealing flange, and the stress unloading oil supply hole communicates with the stress unloading oil chamber; and the stress loading oil supply hole and the stress unloading oil supply hole communicate with the stress loading injection pump by an electromagnetic directional valve.

An auxiliary push-and-pull hydraulic cylinder is arranged in a rigid shell of the pressure chamber, and is arranged in parallel to the cylindrical sample bearing platform, a piston rod of the auxiliary push-and-pull hydraulic cylinder extends to the outer part of the pressure chamber, an adaptor flange is fixedly connected to the end part of the piston rod, the adaptor flange is fixedly connected with the cylindrical sample bearing platform, and the cylindrical sample bearing platform moves axially in the cylindrical through hole by the auxiliary push-and-pull hydraulic cylinder.

A guide hole is formed in the rigid shell of the pressure chamber, a guide rod is arranged in the guide hole, the guide rod is arranged in parallel to the auxiliary push-and-pull hydraulic cylinder, and one end of the guide rod extends to the outer part of the pressure chamber and is fixedly connected with the adaptor flange.

A weight balancing rod is mounted on the cylindrical sample bearing platform on the opposite side of the adaptor flange.

A heating coil is mounted in the pressure chamber, and the temperature control accuracy of the heating coil is ±0.2 DEG C.

A force sensor is fixedly mounted at the end part of the piston rod located in stress loading through holes.

A pressure sensor is mounted in the cylindrical sample bearing platform.

A piston monitoring LVDT (Linear Variable Differential Transformer) displacement sensor is mounted on the sealing cover.

The stress loading injection pumps and the confining pressure loading injection pump all adopt a stepping motor type servo hydraulic injection pump.

A high-pressure true triaxial hard rock constant-temperature time-dependence failure test method, adopting the high-pressure true triaxial hard rock constant-temperature time-dependence failure test apparatus, includes the following steps:

Step I: preparing a rock sample;

Step II: sealing the rock sample;

Step III: enabling a volume change measurement LVDT (Linear Variable Differential Transformer) displacement sensor to be mounted on the surface of the sealed rock sample;

Step IV: starting an auxiliary push-and-pull hydraulic cylinder and moving a cylindrical sample bearing platform to the outer part of a pressure chamber until a sample bearing and containing chamber is located at the outer part of the pressure chamber;

Step V: placing the rock sample which is sealed and is provided with the volume change measurement LVDT displacement sensor into the sample bearing and containing chamber;

Step VI: controlling the auxiliary push-and-pull hydraulic cylinder to retract until the cylindrical sample bearing platform completely returns into a cylindrical through hole of the pressure chamber;

Step VII: implementing displacement control on a first maximum principle stress actuator, a second maximum principle stress actuator, a first intermediate principle stress actuator and a second intermediate principle stress actuator to complete accurate clamping for the rock sample in a centering manner;

Step VIII: adjusting the position of the volume change measurement LVDT displacement sensor and the elongation of a contact probe, so that the volume change measurement LVDT displacement sensor is located within the measuring range of a test;

Step IX: filling the pressure chamber with hydraulic oil;

Step X: starting a heating coil in the pressure chamber to adjust the temperature of the hydraulic oil to target temperature;

Step XI: starting the stress loading injection pumps of the first maximum principle stress actuator, the second maximum principle stress actuator, the first intermediate principle stress actuator and the second intermediate principle stress actuator and starting the confining pressure loading injection pump at the same time, so that stepped true triaxial loading is performed on the rock sample; and Step XII: recording and observing deformation situations of the rock sample under all the stepped-grade loads.

The low-frequency disturbance and high-speed impact type high-pressure true triaxial test apparatus and method disclosed by the present invention have the beneficial effects:

The high-pressure true triaxial hard rock constant-temperature time-dependence failure test apparatus and method disclosed by the present invention have the beneficial effects that: compared with the prior art, a hard rock time-dependence failure test under the true triaxial condition is realized for the first time. In order to meet the requirement for the rock time-dependence failure test under the true triaxial condition, in the high-pressure true triaxial hard rock constant-temperature time-dependence failure test apparatus disclosed by the present invention, a pressure chamber adopting a brand-new structure and actuators adopting a brand-new structure and being assembled with the pressure chamber for application are designed, a stepping motor type servo hydraulic injection pump is introduced into true triaxial loading for the first time, and finally, the high-pressure true triaxial hard rock constant-temperature time-dependence failure test apparatus has the long-time stable loading capacity under the true triaxial condition for the first time through the above innovative design. In addition, in order to ensure that the given stress condition and environment temperature conform to the actual stress condition and environment temperature, oil temperature control is introduced for the first time, so that the requirement of the rock constant-temperature time-dependence failure test can be met, and a truer and more creditable test result is ensured.

According to the high-pressure true triaxial hard rock constant-temperature time-dependence failure test apparatus disclosed by the present invention, the pressure chamber adopts high-rigidity integrated structural design for the first time, the pressure chamber is also served as a counter-force frame of a maximum principle stress and an intermediate principal stress, the actuators assembled with the pressure chamber for application have low-friction large-tonnage loading capacity and have capacity of symmetrically and simultaneously loading the maximum principle stress and the intermediate principal stress, and the maximum loading capacity can reach 6000 kN; the stepping motor type servo hydraulic injection pump introduced by the high-pressure true triaxial hard rock constant-temperature time-dependence failure test apparatus disclosed by the present invention for the first time has capacity of pressure boost and long-time, stable and low-power-consumption loading, the power of a servo motor in the stepping motor type servo hydraulic injection pump can be as low as 1 kW, and confining pressure loading capacity of the stepping motor type servo hydraulic injection pump can reach 100 MPa; and the oil temperature control is introduced for the first time, so that hydraulic oil can be heated for a long time at constant temperature, and a ground temperature condition of a rock sample can be effectively simulated.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
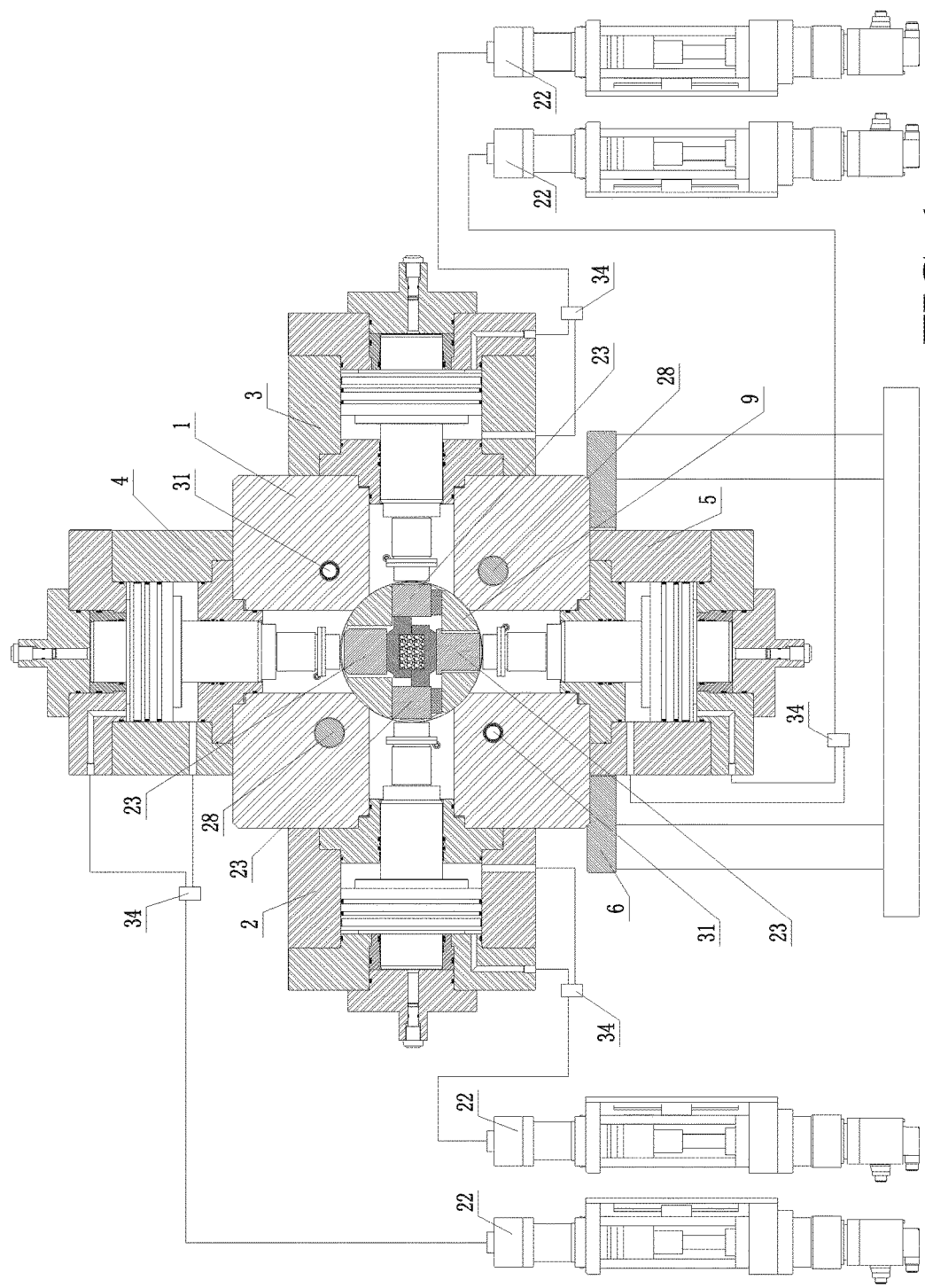
FIG. 1 is a front section view of a high-pressure true triaxial hard rock constant-temperature time-dependence failure test apparatus of the present invention.
Figure 2:
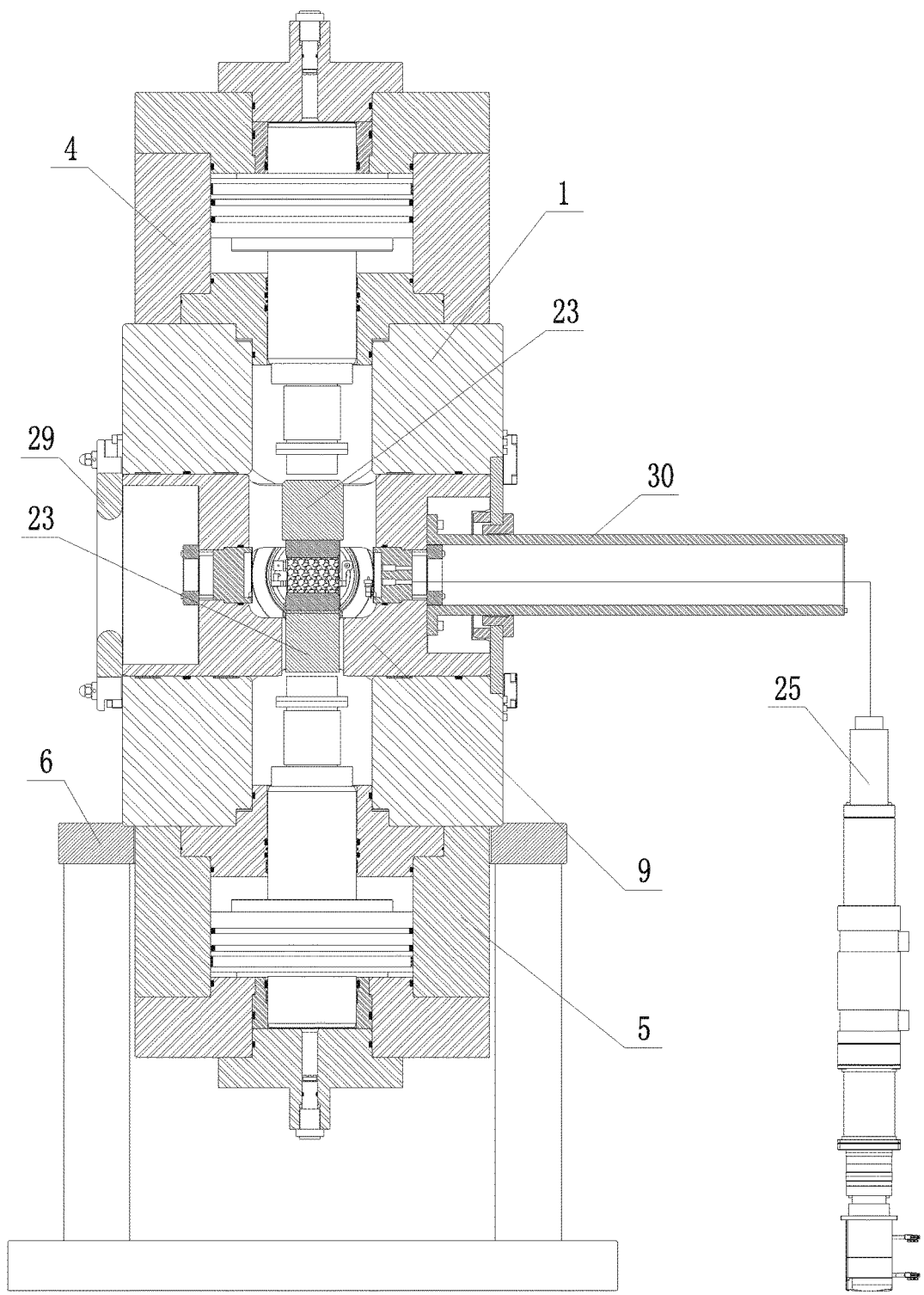
FIG. 2 is a lateral section view of a high-pressure true triaxial hard rock constant-temperature time-dependence failure test apparatus of the present invention.
Figure 3:
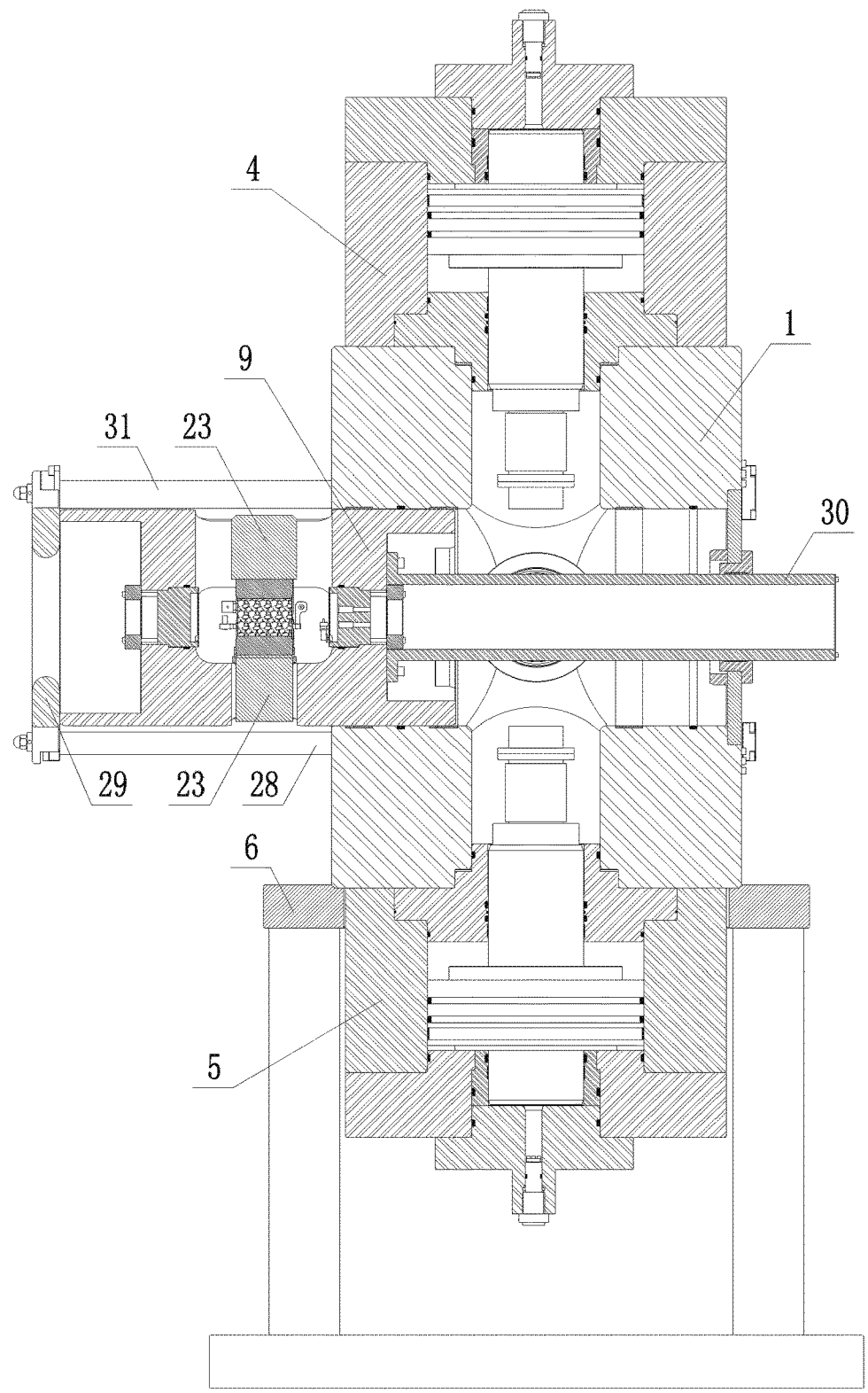
FIG. 3 is a diagram of a cylindrical sample bearing platform in FIG. 2 under the state of being moved out.
Figure 4:
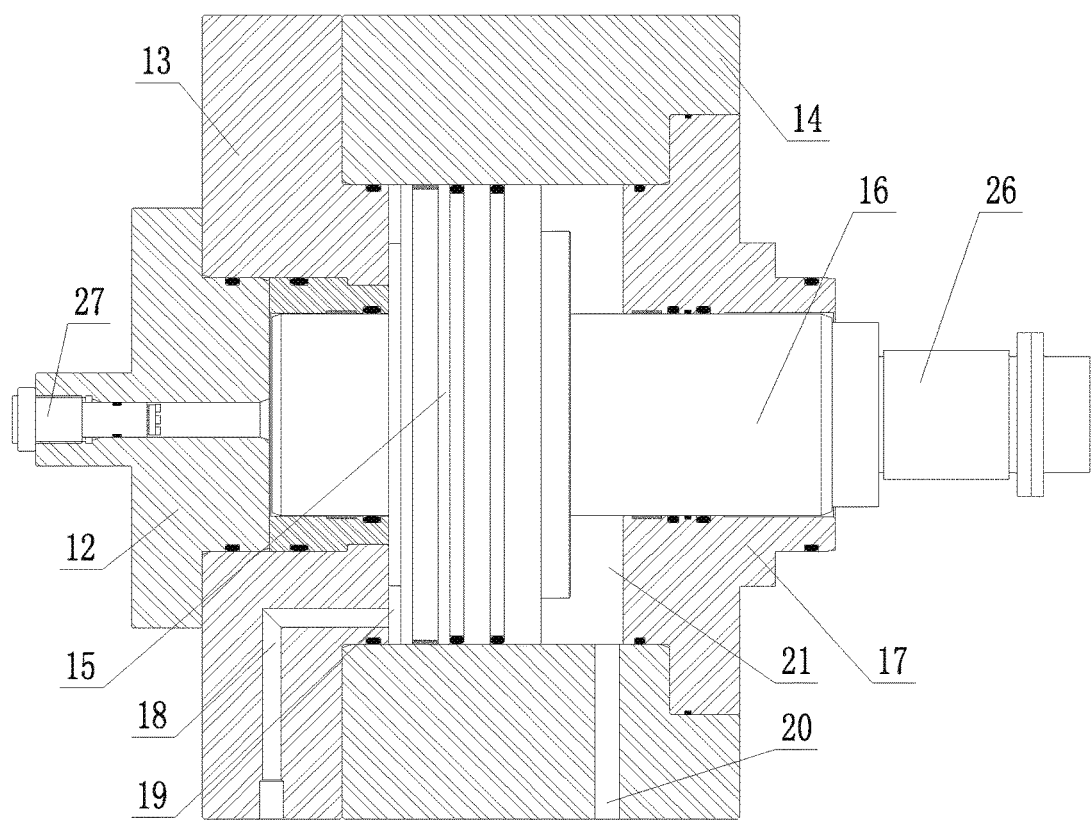
FIG. 4 is a structural schematic diagram of an actuator (a stress loading injection pump is not shown) of the present invention.
Figure 5:
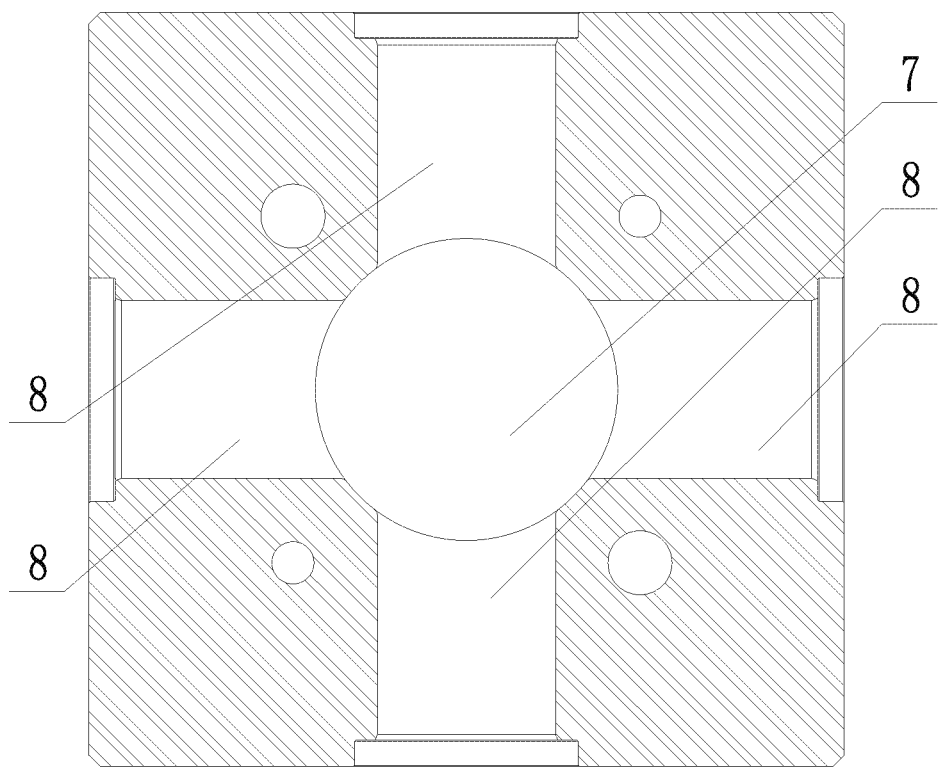
FIG. 5 is a front section view of a pressure chamber of the present invention.
Figure 6:
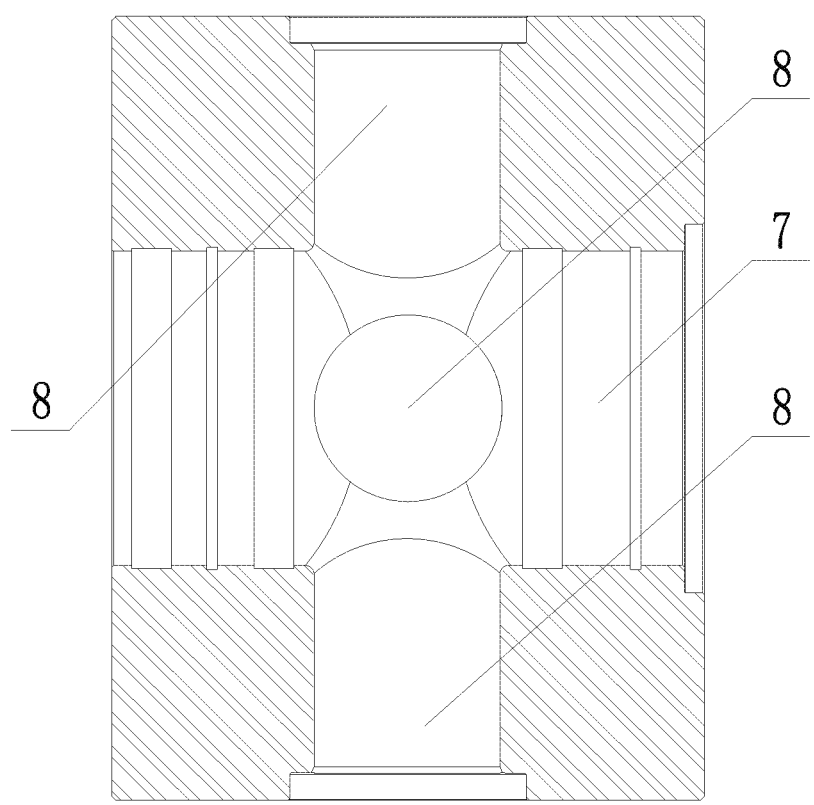
FIG. 6 is a lateral section view of a pressure chamber of the present invention.
Figure 7:
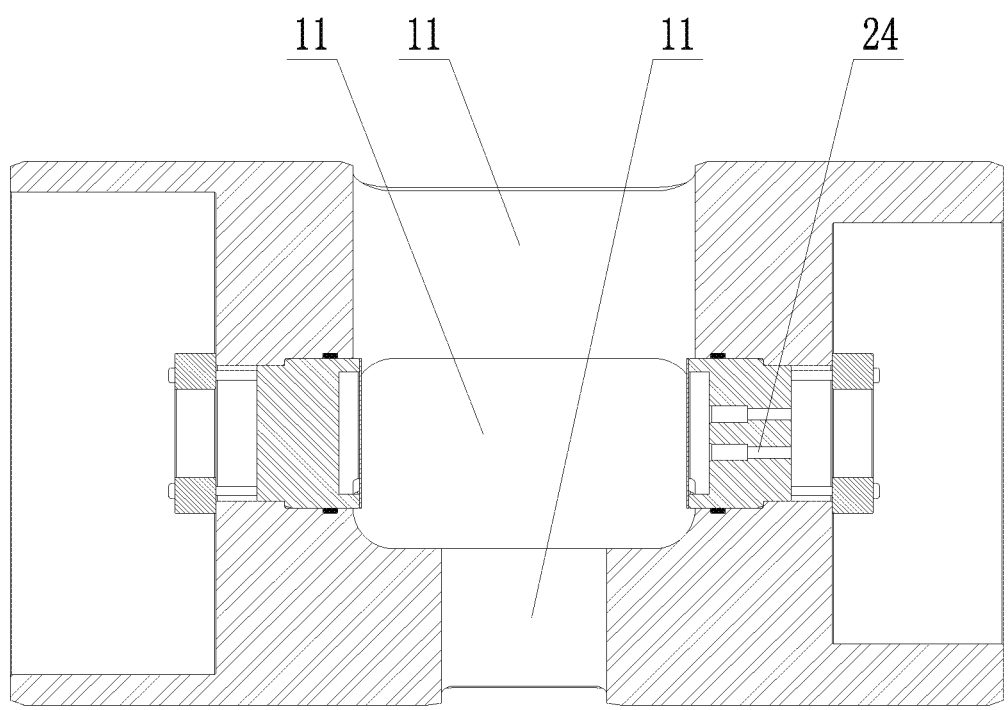
FIG. 7 is a front section view of a cylindrical sample bearing platform of the present invention.
Figure 8:
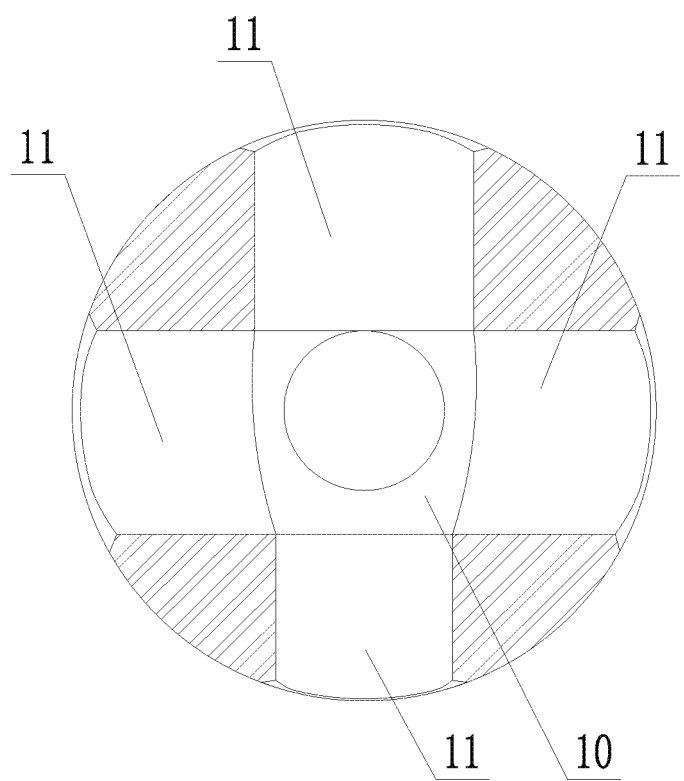
FIG. 8 is a lateral section view of a cylindrical sample bearing platform of the present invention.

The accompanying drawings are included to provide a further understanding of the invention, and are incorporated in and constitute a part of this specification. The drawings illustrate embodiments of the invention and, together with the description, serve to explain the principles of the invention.

As shown in FIGS. 1-8, a high-pressure true triaxial hard rock constant-temperature time-dependence failure test apparatus, includes: a pressure chamber 1, a first maximum principle stress actuator 2, a second maximum principle stress actuator 3, a first intermediate principle stress actuator 4, a second intermediate principle stress actuator 5 and a rigid support platform 6, wherein the pressure chamber 1 is fixedly mounted on the rigid support platform 6, the first maximum principle stress actuator 2 and the second maximum principle stress actuator 3 are horizontally and symmetrically arranged on the left side and the right side of the pressure chamber 1, and the first intermediate principle stress actuator 4 and the second intermediate principle stress actuator 5 are vertically and symmetrically arranged on the upper side and the lower side of the pressure chamber 1;

characterized in that: a cylindrical through hole 7 penetrating horizontally is formed in the center of the pressure chamber 1, four stress loading through holes 8 are uniformly distributed in a rigid shell of the pressure chamber 1, on the upper side, the lower side, the left side and the right side of the cylindrical through hole 7, a cylindrical sample bearing platform 9 is arranged in the cylindrical through hole 7, and is matched with the cylindrical through hole 7 in a sealing manner, and the cylindrical sample bearing platform 9 has axial movement freedom degrees relative to the cylindrical through hole 7; a sample bearing and containing chamber 10 is arranged in the center of the cylindrical sample bearing platform 9, four rigid pressure head placing holes 11 are uniformly distributed in the cylindrical sample bearing platform 9, on the upper side, the lower side, the left side and the right side of the sample bearing and containing chamber 10, the four rigid pressure head placing holes 11 are in one-to-one correspondence to the four stress loading through holes 8, and a rigid pressure head 23 is arranged in each of the four rigid pressure head placing holes 11; a confining pressure loading oil supply hole 24 is formed in the cylindrical sample bearing platform 9 and communicates with the sample bearing and containing chamber 10; the confining pressure loading oil supply hole 24 communicates with a confining pressure loading injection pump 25; the first maximum principle stress actuator 2, the second maximum principle stress actuator 3, the first intermediate principle stress actuator 4 and the second intermediate principle stress actuator 5 have the same structure, and any of the first maximum principle stress actuator 2, the second maximum principle stress actuator 3, the first intermediate principle stress actuator 4 and the second intermediate principle stress actuator 5 includes: a sealing cover 12, an annular end cover 13, a counter-force cylinder barrel 14, a piston 15, a piston rod 16, a sealing flange 17 and a stress loading injection pump 22, wherein the counter-force cylinder barrels 14 are fixedly connected to the outer surface of the pressure chamber 1 and are coincided with axial center lines of the stress loading through holes 8; the sealing cover 12 is fixedly mounted at the middle of the annular end cover 13, the annular end cover 13 is fixedly mounted at the outer end of the counter-force cylinder barrel 14, the sealing flange 17 is fixedly mounted between the inner end of the counter-force cylinder barrel 14 and the pressure chamber 1, one end of the piston rod 16 is located in the counter-force cylinder barrel 14, the other end of the piston rod 16 penetrates through the sealing flange 17 and extends into the stress loading through holes 8, the piston 15 is located in the counter-force cylinder barrel 14 and is fixedly arranged on the piston rod 16 in a sleeving manner, and the piston 15 is matched with the counter-force cylinder barrel 14 in a sealing and sliding manner; a stress loading oil supply hole 18 is formed on the annular end cover 13, a stress loading oil chamber 19 is arranged between the annular end cover 13 and the piston 15, and the stress loading oil supply hole 18 communicates with the stress loading oil chamber 19; a stress unloading oil supply hole 20 is formed on the counter-force cylinder barrel 14, a stress unloading oil chamber 21 is arranged between the piston 15 and the sealing flange 17, and the stress unloading oil supply hole 20 communicates with the stress unloading oil chamber 21; and the stress loading oil supply hole 18 and the stress unloading oil supply hole 20 communicate with the stress loading injection pump 22 by an electromagnetic directional valve 34.

According to the high-pressure true triaxial hard rock constant-temperature time-dependence failure test apparatus and method disclosed by the present invention, a pressure chamber 1 adopts a high-rigidity integrated structural design, the pressure chamber 1 is served as a counter-force frame of a maximum principle stress and an intermediate principal stress, and the design of the pressure chamber 1 is completely different from the design of three elements of two loading frames and one pressure chamber 1, which are adopted in the traditional true triaxial equipment. Due to the high-rigidity integrated structural design, the pressure chamber has small size, further enhancement of rigidity is facilitated, the rigidity of the rock sample can be well matched, and the problems of mounting spaces and mounting errors among the three elements in the traditional true triaxial equipment are effectively solved.

An auxiliary push-and-pull hydraulic cylinder 28 is arranged in a rigid shell of the pressure chamber 1, and is arranged in parallel to the cylindrical sample bearing platform 9, a piston rod of the auxiliary push-and-pull hydraulic cylinder 28 extends to the outer part of the pressure chamber 1, an adaptor flange 29 is fixedly connected to the end part of the piston rod, the adaptor flange 29 is fixedly connected with the cylindrical sample bearing platform 9, and the cylindrical sample bearing platform 9 moves axially in the cylindrical through hole 7 by the auxiliary push-and-pull hydraulic cylinder 28.

The cylindrical sample bearing platform 9 of the high-pressure true triaxial hard rock constant-temperature time-dependence failure test apparatus disclosed by the present invention moves axially in the cylindrical through hole 7 of the pressure chamber 1 by the auxiliary push-and-pull hydraulic cylinder 28, so that requirements for quick loading and taking of the rock sample can be met. The conventional pressure chamber adopts a bolt locking type sealing door, the sealing door needs to be disassembled and assembled once for sample loading and taking each time, which is heavy manual work for test personnel, and the process of heavy manual work is completely omitted in the high-pressure true triaxial hard rock constant-temperature time-dependence failure test apparatus and method.

A guide hole is formed in the rigid shell of the pressure chamber 1, a guide rod 31 is arranged in the guide hole, the guide rod 31 is arranged in parallel to the auxiliary push-and-pull hydraulic cylinder 28, and one end of the guide rod 31 extends to the outer part of the pressure chamber 1 and is fixedly connected with the adaptor flange 29.

A weight balancing rod 30 is mounted on the cylindrical sample bearing platform 9 on the opposite side of the adaptor flange 29. When the cylindrical sample bearing platform 9 moves outwards along the cylindrical through hole 7, the extending part of the cylindrical sample bearing platform 9 can damage the cylindrical through hole 7 due to dead weight as the moving-out distance is increased, and the dead weight of the extending part of the cylindrical sample bearing platform 9 can be counteracted by a weight balancing rod 30, so that damage to the cylindrical through hole 7 is avoided.

A heating coil is mounted in the pressure chamber 1, and the temperature control accuracy of the heating coil is ±0.2 DEG C.; and hydraulic oil is served as a cold medium, so that ensuring of the temperature control accuracy is facilitated.

A force sensor 26 is fixedly mounted at the end part of a piston rod 16 located in stress loading through holes 8; and the force sensor 26 is located in the stress loading through holes 8, and compared with the situation that the force sensor 26 in the existing true triaxial equipment is usually arranged outside the pressure chamber, influence of fluctuation of environment temperature and influence of friction of a force-transferring piston are eliminated, so that long-time load stable control is facilitated.

A pressure sensor is mounted in the cylindrical sample bearing platform 9.

A piston monitoring LVDT (Linear Variable Differential Transformer) displacement sensor 27 is mounted on the sealing cover 12.

The stress loading injection pumps 22 and the confining pressure loading injection pump 25 all adopt a stepping motor type servo hydraulic injection pump; and in the embodiment, the highest output pressure of a stepping motor type servo hydraulic injection pump being selected is 100 MPa, and the lowest output rate is 0.0005 ml/min. Because the power of a servo motor in the stepping motor type servo hydraulic injection pump is lower, the temperature rising speed of hydraulic oil in a pump cylinder can be effectively decreased; in addition, a speed changing box with a large reduction ratio in the stepping motor type servo hydraulic injection pump can also ensure low-speed movement of a piston of the pump cylinder, and the stepping motor type servo hydraulic injection pump is more suitable for the characteristic of small deformation of a hard rock; and besides, a stepping motor controller and a load feedback double closed-loop control technology are adopted, so that long-time constant load control is facilitated.

Figure 9:
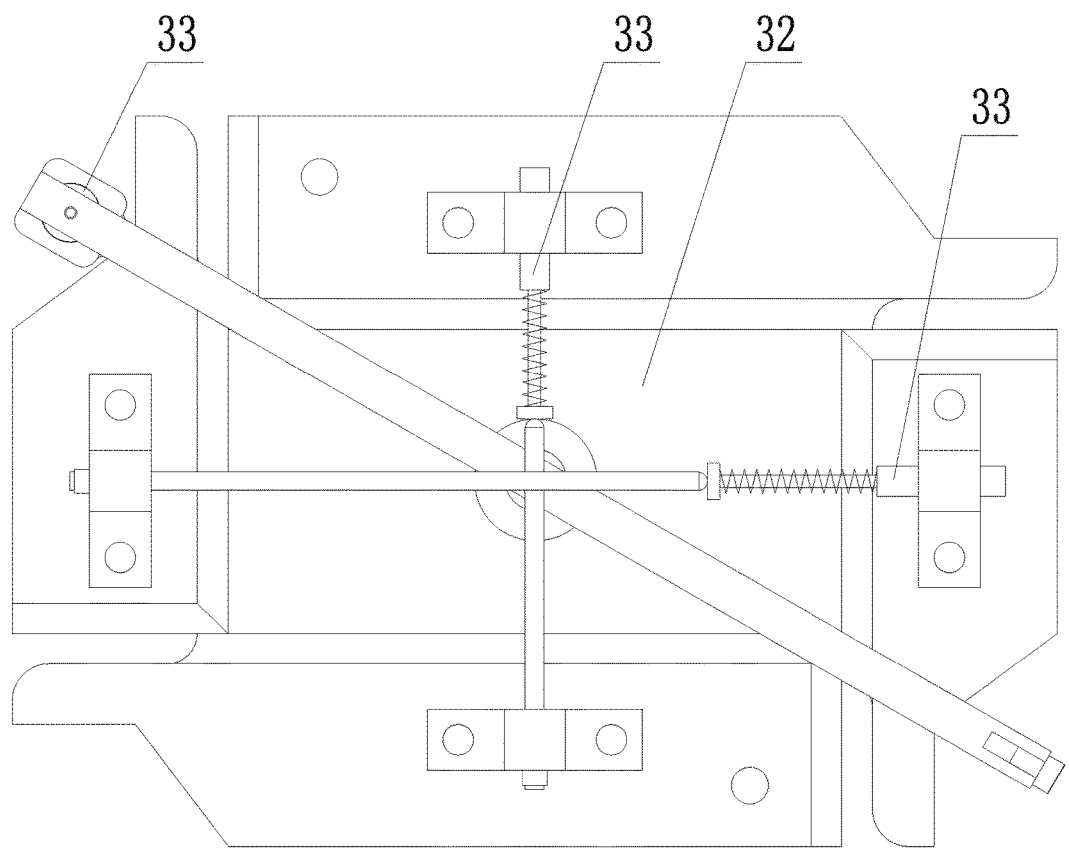
FIG. 9 is a schematic diagram of a rock sample which is sealed and is provided with a volume change measurement LVDT (Linear Variable Differential Transformer) displacement sensor, wherein in the figures, 1=pressure chamber, 2=first maximum principle stress actuator, 3=second maximum principle stress actuator, 4=first intermediate principle stress actuator, 5=second intermediate principle stress actuator, 6=rigid support platform, 7=cylindrical through hole, 8=stress loading through hole, 9=cylindrical sample bearing platform, 10=sample bearing and containing chamber, 11=rigid pressure head placing hole, 12=sealing cover, 13=annular end cover, 14=counter-force cylinder barrel, 15=piston, 16=piston rod, 17=sealing flange, 18=stress loading oil supply hole, 19=stress loading oil chamber, 20=stress unloading oil supply hole, 21=stress unloading oil chamber, 22=stress loading injection pump, 23=rigid pressure head, 24=confining pressure loading oil supply hole, 25=confining pressure loading injection pump, 26=force sensor, 27=piston monitoring LVDT displacement sensor, 28=auxiliary push-and-pull hydraulic cylinder, 29=adaptor flange, 30=weight balancing rod, 31=guide rod, 32=rock sample, 33=volume change measurement LVDT displacement sensor and 34=electromagnetic directional valve.

A high-pressure true triaxial hard rock constant-temperature time-dependence failure test method, adopting the high-pressure true triaxial hard rock constant-temperature time-dependence failure test apparatus, includes the following steps:

Step I: preparing a rock sample 32, wherein the final dimension of the rock sample 32 is 50 mm*50 mm*100 mm;

Step II: sealing the rock sample 32;

Step III: enabling a volume change measurement LVDT (Linear Variable Differential Transformer) displacement sensor 33 to be mounted on the surface of the sealed rock sample 32, As shown in FIG. 9;

Step IV: starting an auxiliary push-and-pull hydraulic cylinder 28 and moving a cylindrical sample bearing platform 9 to the outer part of a pressure chamber 1 until a sample bearing and containing chamber 10 is located at the outer part of the pressure chamber 1;

Step V: placing the rock sample 32 which is sealed and is provided with the volume change measurement LVDT displacement sensor 33 into the sample bearing and containing chamber 10;

Step VI: controlling the auxiliary push-and-pull hydraulic cylinder 28 to retract until the cylindrical sample bearing platform 9 completely returns into a cylindrical through hole 7 of the pressure chamber 1;

Step VII: implementing displacement control on a first maximum principle stress actuator 2, a second maximum principle stress actuator 3, a first intermediate principle stress actuator 4 and a second intermediate principle stress actuator 5 to complete accurate clamping for the rock sample 32 in a centering manner;

Step VIII: adjusting the position of the volume change measurement LVDT displacement sensor 33 and the elongation of a contact probe, so that the volume change measurement LVDT displacement sensor 33 is located within the measuring range of a test;

Step IX: filling the pressure chamber 1 with hydraulic oil;

Step X: starting a heating coil in the pressure chamber 1 to adjust the temperature of the hydraulic oil to target temperature, and in the embodiment, the highest controlled temperature of the heating coil is set as 100 DEG C.;

Step XI: starting the stress loading injection pumps 22 of the first maximum principle stress actuator 2, the second maximum principle stress actuator 3, the first intermediate principle stress actuator 4 and the second intermediate principle stress actuator 5 and starting the confining pressure loading injection pump 25 at the same time, so that stepped true triaxial loading is performed on the rock sample 32; in the embodiment, in consideration of safety, maximum output loads of the first maximum principle stress actuator 2 and the second maximum principle stress actuator 3 are set as 3000 kN, maximum output loads of the first intermediate principle stress actuator 4 and the second intermediate principle stress actuator 5 are set as 6000 kN, and a maximum load of the confining pressure is set as 100 MPa; and Step XII: recording and observing deformation situations of the rock sample 32 under all the stepped-grade loads.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A test apparatus for determining time-dependence failure under constant temperature through high pressure true triaxial loading for hard rock, comprising:

a pressure chamber, a first maximum principle stress actuator, a second maximum principle stress actuator, a first intermediate principle stress actuator, a second intermediate principle stress actuator and a rigid support platform, wherein the pressure chamber is fixedly mounted on the rigid support platform, the first maximum principle stress actuator and the second maximum principle stress actuator are horizontally and symmetrically arranged on the left side and the right side of the pressure chamber, and the first intermediate principle stress actuator and the second intermediate principle stress actuator are vertically and symmetrically arranged on the upper side and the lower side of the pressure chamber; wherein a cylindrical through hole penetrating horizontally is formed in a center of the pressure chamber, four stress loading through holes are uniformly distributed in a rigid shell of the pressure chamber, on the upper side, the lower side, the left side and the right side of the cylindrical through hole, a cylindrical sample bearing platform is arranged in the cylindrical through hole, and is matched with the cylindrical through hole in a sealing manner, and the cylindrical sample bearing platform has axial movement freedom degrees relative to the cylindrical through hole;

a sample bearing and containing chamber is arranged in a center of the cylindrical sample bearing platform, four rigid pressure head placing holes are uniformly distributed in the cylindrical sample bearing platform, on the upper side, the lower side, the left side and the right side of the sample bearing and containing chamber, the four rigid pressure head placing holes are in one-to-one correspondence to the four stress loading through holes, and a rigid pressure head is arranged in each of the four rigid pressure head placing holes; a confining pressure loading oil supply hole is formed in the cylindrical sample bearing platform and communicates with the sample bearing and containing chamber; the confining pressure loading oil supply hole communicates with a confining pressure loading injection pump;

the first maximum principle stress actuator, the second maximum principle stress actuator, the first intermediate principle stress actuator and the second intermediate principle stress actuator have the same structure, and any of the first maximum principle stress actuator, the second maximum principle stress actuator, the first intermediate principle stress actuator and the second intermediate principle stress actuator includes: a sealing cover, an annular end cover, a counter-force cylinder barrel, a piston, a piston rod, a sealing flange and a stress loading injection pump, wherein the counter-force cylinder barrels are fixedly connected to the outer surface of the pressure chamber and are coincided with axial center lines of the stress loading through holes; the sealing cover is fixedly mounted at the middle of the annular end cover, the annular end cover is fixedly mounted at the outer end of the counter-force cylinder barrel, the sealing flange is fixedly mounted between the inner end of the counter-force cylinder barrel and the pressure chamber, one end of the piston rod is located in the counter-force cylinder barrel, the other end of the piston rod penetrates through the sealing flange and extends into the stress loading through holes, the piston is located in the counter-force cylinder barrel and is fixedly arranged on the piston rod in a sleeving manner, and the piston is matched with the counter-force cylinder barrel in a sealing and sliding manner; a stress loading oil supply hole is formed on the annular end cover, a stress loading oil chamber is arranged between the annular end cover and the piston, and the stress loading oil supply hole communicates with the stress loading oil chamber; a stress unloading oil supply hole is formed on the counter-force cylinder barrel, a stress unloading oil chamber is arranged between the piston and the sealing flange, and the stress unloading oil supply hole communicates with the stress unloading oil chamber; and the stress loading oil supply hole and the stress unloading oil supply hole communicate with the stress loading injection pump by an electromagnetic directional valve;

an auxiliary push-and-pull hydraulic cylinder is arranged in a rigid shell of the pressure chamber, and is arranged in parallel to the cylindrical sample bearing platform, a piston rod of the auxiliary push-and-pull hydraulic cylinder extends to the outer part of the pressure chamber, an adaptor flange is fixedly connected to the end part of the piston rod, the adaptor flange is fixedly connected with the cylindrical sample bearing platform, and the cylindrical sample bearing platform moves axially in the cylindrical through hole by the auxiliary push-and-pull hydraulic cylinder.

2. The test apparatus according to claim 1, wherein a guide hole is formed in the rigid shell of the pressure chamber, a guide rod is arranged in the guide hole, the guide rod is arranged in parallel to the auxiliary push-and-pull hydraulic cylinder, and one end of the guide rod extends to the outer part of the pressure chamber and is fixedly connected with the adaptor flange.

3. The test apparatus according to claim 1, wherein a weight balancing rod is mounted on the cylindrical sample bearing platform on the opposite side of the adaptor flange.

4. The test apparatus according to claim 1, wherein a heating coil is mounted in the pressure chamber, and the temperature control accuracy of the heating coil is ±0.2 DEG C.

5. The test apparatus according to claim 1, wherein a force sensor is fixedly mounted at the end part of the piston rod located in stress loading through holes.

6. The test apparatus according to claim 1, wherein a pressure sensor is mounted in the cylindrical sample bearing platform.

7. The test apparatus according to claim 1, wherein a piston monitoring LVDT (Linear Variable Differential Transformer) displacement sensor is mounted on the sealing cover.

8. The test apparatus according to claim 1, wherein the stress loading injection pumps and the confining pressure loading injection pump all adopt a stepping motor type servo hydraulic injection pump.

9. A test method for determining time-dependence failure under constant temperature through high pressure true triaxial loading for hard rock by adopting the test apparatus according to claim 1, comprising the following steps:
Step I: preparing a rock sample;
Step II: sealing the rock sample;
Step III: enabling a volume change measurement LVDT (Linear Variable Differential Transformer) displacement sensor to be mounted on the surface of the sealed rock sample;
Step IV: starting an auxiliary push-and-pull hydraulic cylinder and moving a cylindrical sample bearing platform to the outer part of a pressure chamber until a sample bearing and containing chamber is located at the outer part of the pressure chamber;
Step V: placing the rock sample which is sealed and is provided with the volume change measurement LVDT displacement sensor into the sample bearing and containing chamber;
Step VI: controlling the auxiliary push-and-pull hydraulic cylinder to retract until the cylindrical sample bearing platform completely returns into a cylindrical through hole of the pressure chamber;
Step VII: implementing displacement control on a first maximum principle stress actuator, a second maximum principle stress actuator, a first intermediate principle stress actuator and a second intermediate principle stress actuator to complete accurate clamping for the rock sample in a centering manner;
Step VIII: adjusting the position of the volume change measurement LVDT displacement sensor and the elongation of a contact probe, so that the volume change measurement LVDT displacement sensor is located within the measuring range of a test;
Step IX: filling the pressure chamber with hydraulic oil;
Step X: starting a heating coil in the pressure chamber to adjust the temperature of the hydraulic oil to target temperature;
Step XI: starting the stress loading injection pumps of the first maximum principle stress actuator, the second maximum principle stress actuator, the first intermediate principle stress actuator and the second intermediate principle stress actuator and starting the confining pressure loading injection pump at the same time, so that stepped true triaxial loading is performed on the rock sample; and
Step XII: recording and observing deformation situations of the rock sample under all the stepped-grade loads.

* * * * *